United States Patent
Mueller et al.

(10) Patent No.: US 8,568,381 B2
(45) Date of Patent: Oct. 29, 2013

(54) TAMPON AND A METHOD OF PRODUCING A TAMPON

(75) Inventors: Peter Mueller, Zurich (CH); Kilian Rolli, Wuerenlingen (CH)

(73) Assignee: Ruggli Projects AG, Hagendorn (CH)

( * ) Notice: Subject to any disclaimer, the term of this patent is extended or adjusted under 35 U.S.C. 154(b) by 703 days.

(21) Appl. No.: 12/451,796

(22) PCT Filed: May 30, 2008

(86) PCT No.: PCT/EP2008/004289
§ 371 (c)(1),
(2), (4) Date: Dec. 8, 2009

(87) PCT Pub. No.: WO2008/145370
PCT Pub. Date: Dec. 4, 2008

(65) Prior Publication Data
US 2010/0114054 A1    May 6, 2010

(30) Foreign Application Priority Data
Jun. 1, 2007 (DE) .......... 10 2007 025 783

(51) Int. Cl.
*A61F 13/15* (2006.01)
(52) U.S. Cl.
USPC .......... 604/385.18; 604/904; 28/120
(58) Field of Classification Search
USPC .......... 604/385.18, 904; 28/118–120
See application file for complete search history.

(56) References Cited

U.S. PATENT DOCUMENTS

| | | | | |
|---|---|---|---|---|
| 3,431,909 A | * | 3/1969 | Krusko | 604/15 |
| 3,610,243 A | * | 10/1971 | Jones, Sr. | 604/375 |
| 3,845,767 A | * | 11/1974 | Friese et al. | 604/385.18 |
| 4,222,381 A | * | 9/1980 | Widlund et al. | 604/365 |
| 4,642,108 A | | 2/1987 | Sustmann | |
| 4,816,100 A | | 3/1989 | Friese | |
| 4,859,273 A | | 8/1989 | Friese | |

(Continued)

FOREIGN PATENT DOCUMENTS

| | | |
|---|---|---|
| CA | 2 396 475 | 6/2001 |
| DE | 818 234 | 10/1951 |

(Continued)

OTHER PUBLICATIONS

International Search Report.

*Primary Examiner* — Lynne Anderson
(74) *Attorney, Agent, or Firm* — Collard & Roe, P.C.

(57) ABSTRACT

A tampon is proposed, with an insertion end and a rear end, made from a pressed absorbent strip (2) and a withdrawal string (3) running out of the rear end. In order to achieve short production times during manufacture of the tampon, the withdrawal string (3) is placed around the strip (2) in the shape of a loop 4, and the strip (2) is provided with a fold (16, 17) at each side of the loop (4).

Figure 1:
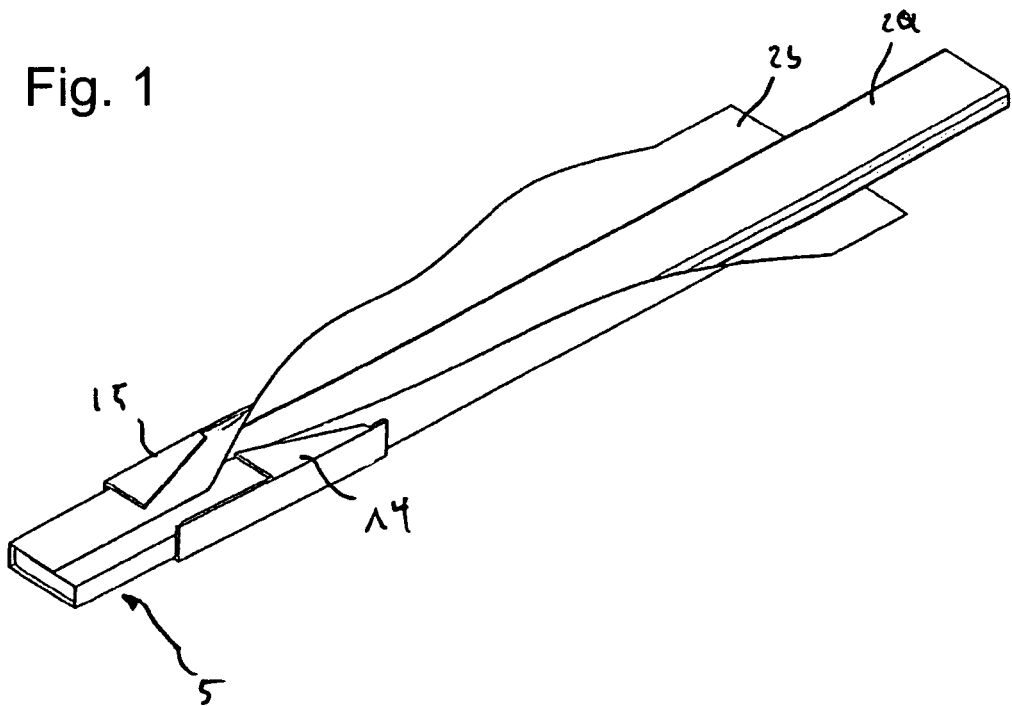

In terms of a method suitable for producing a tampon, the following steps are proposed:
a) cutting the absorbent strip (2) to size,
b) placing a withdrawal string (3) around the strip (2) in the shape of a loop (4),
c) pressing the strip (2) between jaws (7) which can be moved towards one another forming a fold (16, 17) in the strip (2) on each side of the loop (4).

11 Claims, 3 Drawing Sheets

(56) References Cited

U.S. PATENT DOCUMENTS

| | | |
|---|---|---|
| 4,863,450 A | 9/1989 | Friese |
| 6,186,994 B1 * | 2/2001 | Bowles et al. ............ 604/385.17 |
| 6,719,743 B1 | 4/2004 | Wada |
| 6,887,226 B2 | 5/2005 | Cassoni et al. |
| 2005/0027275 A1 | 2/2005 | Wasson et al. |
| 2007/0016156 A1 | 1/2007 | Burgdorf et al. |
| 2007/0191805 A1 | 8/2007 | Kramer |

FOREIGN PATENT DOCUMENTS

| | | |
|---|---|---|
| DE | 32 36 540 | 4/1984 |
| DE | 33 47 649 | 7/1985 |
| DE | 202 01 882 | 7/2002 |
| DE | 200 22 800 | 8/2002 |
| DE | 103 16 234 | 11/2004 |
| EP | 0 149 155 | 7/1985 |
| EP | 1 108 407 | 6/2001 |

* cited by examiner

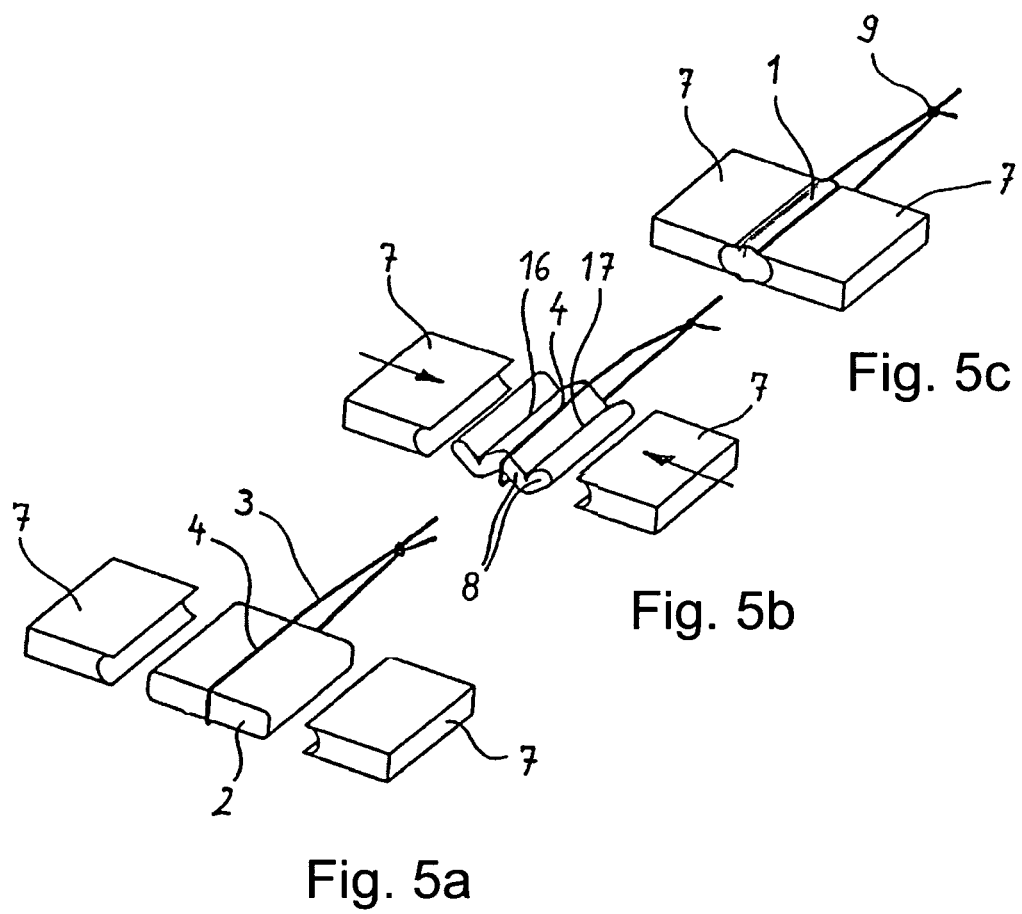

TAMPON AND A METHOD OF PRODUCING A TAMPON

CROSS REFERENCE TO RELATED APPLICATIONS

This application is the National Stage of PCT/EP2008/004289 filed on May 30, 2008, which claims priority under 35 U.S.C. §119 of German Application No. 10 2007 025 783.1 filed on Jun. 1, 2007. The international application under PCT article 21(2) was not published in English.

This invention relates to a tampon with an insertion end and a rear end, made from a pressed absorbent strip and a withdrawal string running out from the rear end. The invention further relates to a method of producing a tampon made from an absorbent strip joined to a withdrawal string.

In the case of so-called applicator tampons used these days, where the actual tampon is disposed inside a sleeve and is applied by pushing a ram, the withdrawal string needed for subsequently removing the used tampon is attached to the absorbent material of the tampon by stitching. During the process of producing the tampon, an absorbent strip is used as the initial material, to which the withdrawal string is stitched. In a subsequent step, the tampon is then shaped from the initial strip shape into the final, approximately cylindrical shape under the effect of pressure.

Stitching the withdrawal string to the absorbent strip of the tampon has proved to be problematic. The reason is that there are limits on the sewing machines due to the stitching speeds which can be achieved, which means that it is not possible to increase the production rates of tampon manufacture beyond the speed of the sewing machine with a view to obtaining short production times.

Accordingly, the objective of this invention is to propose a tampon and a method of manufacturing it which is based on short production times.

To achieve this objective, as far as the tampon is concerned, it is proposed that the withdrawal string be wrapped around the strip in the form of a loop and that the strip be provided with a fold on each side of the loop.

By attaching the withdrawal string to the absorbent strip by forming a loop wrapped around the strip, high production speeds and cycle times can be achieved when manufacturing the applicator tampon. The loop temporarily secures the withdrawal string. During the subsequent process of pressing the applicator tampon, folds are formed in the material of the strip, and these folds restrict the ability of the withdrawal string to move, as a result of which the string can no longer slip or disappear during this phase.

Joining processes such as a welding process, for example, may be considered as a means of securing the withdrawal string more effectively. Welding by means of heated pressing pieces, by ultrasound, laser etc., is particularly suitable for this purpose. However, bonding would also be a suitable process for joining the withdrawal string to the strip prior to shaping.

The absorbent strip is advantageously made up of a liquid-storing strip of fiber, non-woven material or wadding and a sheath surrounding it. The strip of fiber disposed in the interior of the strip stores the liquid which passes through the sheath.

To impart tensile strength to the join between the withdrawal string and strip, it is also of advantage if the withdrawal string is welded or bonded along both the top face of the strip and its bottom face.

In terms of the method, the, above-mentioned objective is achieved by a method of producing a tampon from an absorbent strip joined to a withdrawal string comprising the following steps:

a) cutting the absorbent strip to size,
b) placing a withdrawal string around the strip in the shape of a loop,
c) pressing the strip between jaws which can be moved towards one another, forming a fold in the strip on each side of the loop.

This method enables a significantly higher production rate, i.e. a shorter manufacturing time per tampon, to be achieved than is the case with the prior art.

Figure 2:
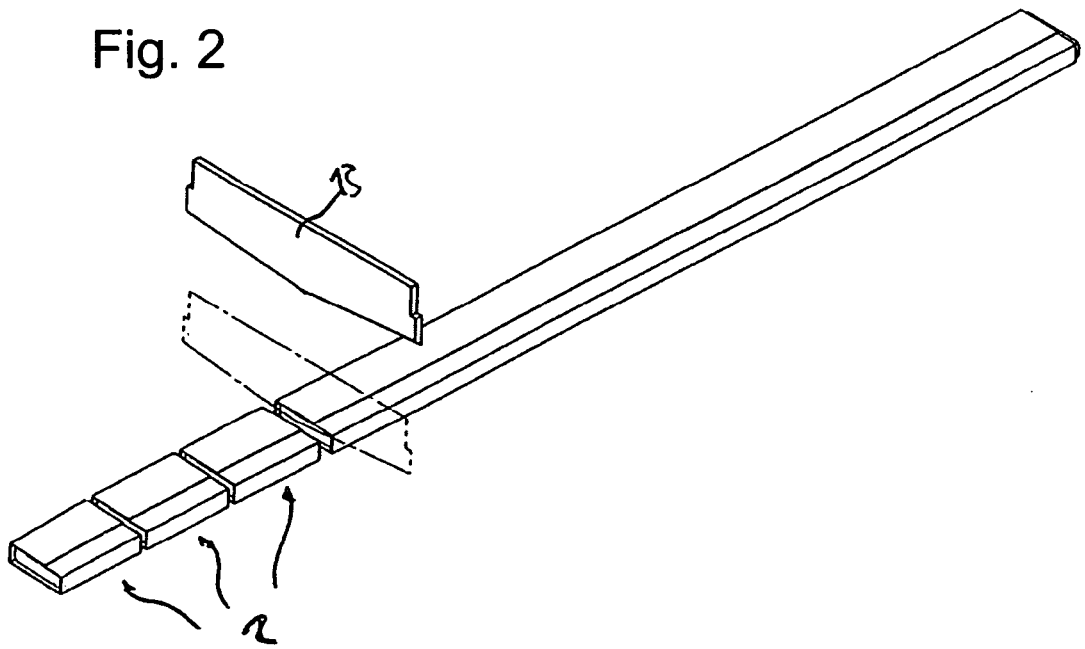
Figure 3:
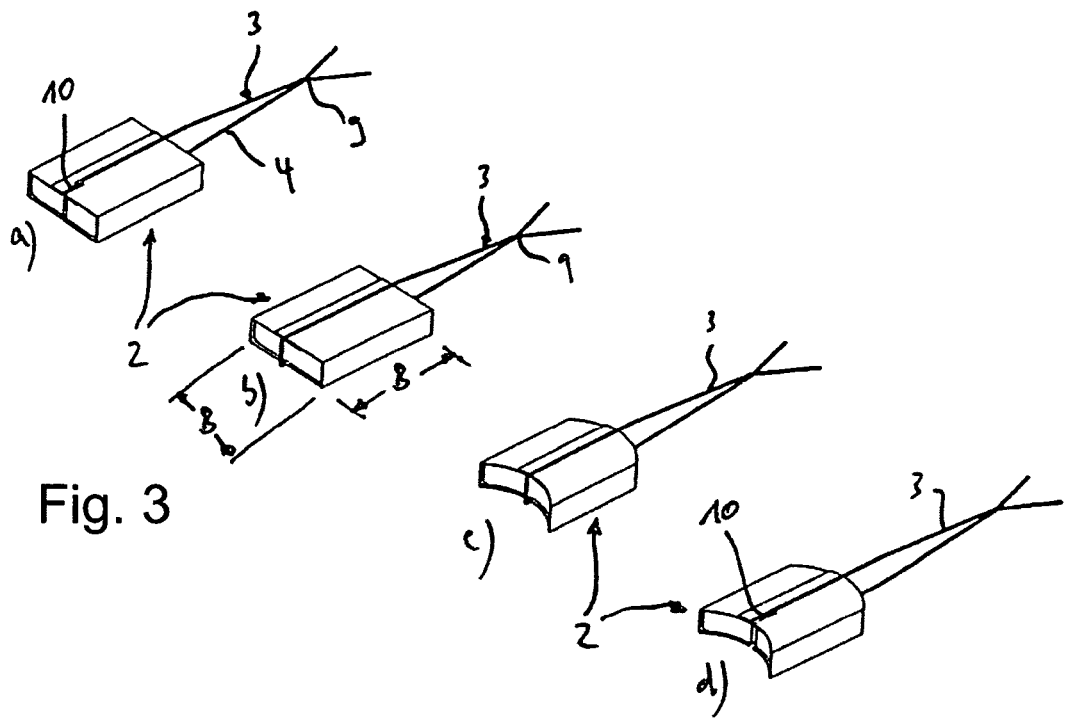
Figure 4:
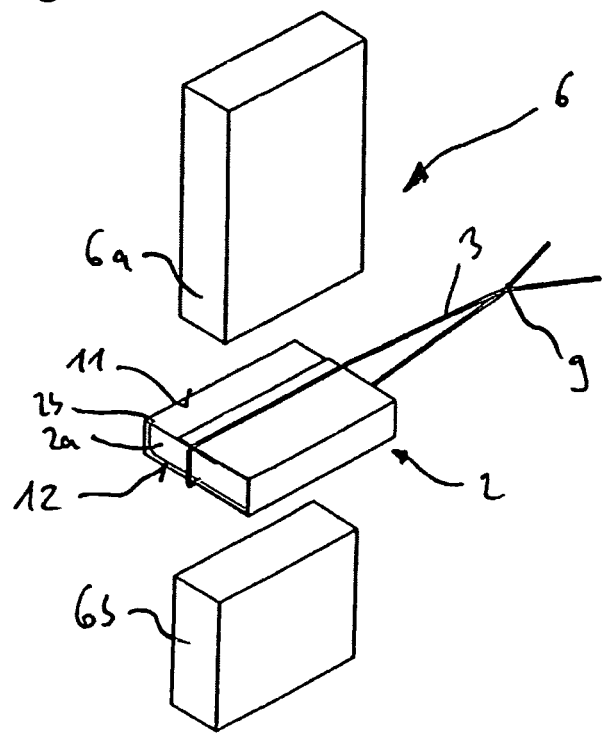

Other details and advantages of the tampon proposed by the invention and the method of producing it proposed by the invention will be explained below with reference to the appended drawings. Of these:

FIG. 1 is a perspective diagram illustrating the production of an endless material, from which FIG. 2 individual absorbent strips are cut to size, FIG. 3 illustrates four different strip geometries (FIGS. 3a to 3d), FIG. 4 is a perspective view illustrating how the withdrawal string is welded to the strip, FIG. 5 illustrates how the applicator tampon is shaped by pressure sources directed towards one another in individual stages (FIGS. 5a, 5b and 5c).

FIG. 1, firstly, illustrates the production of an endless material 5, from which absorbent strips 2 are cut in subsequent production steps to produce a tampon 1 which will be inserted in a tampon applicator. The endless material 5 is made from a fiber strip or wadding strip 2a which is absorbent to liquids and a sheath 2b surrounding the strip. The wadding strip 2a has an approximately polygonal or oval cross-section, whereas the sheath 2b is a relatively thin film or membrane which is permeable to liquid. The fiber or wadding strips 2a is sheathed by a relative movement of the wadding strip 2a and the film 2b with respect to two contact jaws 14, 15, as a result of which the sheath 2b is wrapped around the wadding strip 2a in a manner similar to that in which tinfoil is wrapped around a stick of chewing gum.

Prepared in this manner, the endless material 5 is fed to one or alternatively several cutters 13 which cut the absorbent strip 2 from the endless material 5 in the next production step. As cutters 13, it would be conceivable to use a plurality of different cutters or alternatively differing arrangements of cutters.

The geometry of several absorbent strips 2 is illustrated in FIGS. 3a to 3d. The strips 2 illustrated in FIGS. 3a and 3b are approximately cube-shaped, and the strip illustrated in FIG. 3a is provided with a short slit 10 extending in the longitudinal direction of the strip at one end for clamping a withdrawal string 3 placed in the shape of a loop 4.

The loop 4 is clamped in the region of the point where it is turned back on itself. The strip 2 illustrated in FIG. 3d is also provided with such a slit or alternatively with a notch 10. Unlike the strips 2 illustrated in FIGS. 3a and 3b, the strip 2s illustrated in FIGS. 3c and 3d are not of a cube-rectangular shape but are more or less shovel-shaped.

All the strips 2 have a length L and a width B. As may also be seen from FIG. 3, the withdrawal string 3 placed in a loop 4 approximately at the centre of the width B is provided with a knot 9 at its rear, free end. This results in a closed loop, which is looped around the absorbent strip 2 in the longitudinal direction, i.e. the absorbent strip 2 is disposed inside the loop. Once the absorbent strip 2 and the withdrawal string 3 have been prepared in this manner and positioned relative to one another, they can additionally be joined to one another in the next production step.

To this end, FIG. 4 illustrates an arrangement used to weld the withdrawal string 3 to the absorbent strip 2. In the embodiment illustrated as an example, welding takes place by means of a heated pressing piece 6a, 6b of a welding apparatus 6 disposed respectively above and underneath the strip 2. By means of the mutually facing pressing surfaces of the pressing pieces 6a, 6b, the withdrawal string 3 is subjected to a defined force under the effect of temperature until a welded join is created between the absorbent strip 2 and withdrawal string 3. Depending on the welding parameters selected, such as pressure, temperature, welding time, etc., the withdrawal string 3 may be welded to only the non-woven material of the sheath 2b or alternatively to the wadding strip 2a as well. As may also be seen from FIG. 4, the withdrawal string 3 is welded along the top face 11 and the bottom face 12 of the absorbent strip 2. It would also be conceivable to opt for arrangements whereby only one thread is welded to either the top or the bottom face, for example. Instead of welding, it would also be possible to use a bonding process, for example.

FIGS. 5a to 5c illustrate how the absorbent strip 2 is transformed from its cube or shovel shape into an essentially cylindrical shape in three stages. During a first step (FIG. 5a), the absorbent strip 2 with the withdrawal string 3 disposed centrally on it and optionally secured by welding is positioned between two pressing jaws 7 of a press which can be moved radially towards one another. The absorbent strip 2 is then pressed into an approximately cylindrical shape as illustrated in FIGS. 5b and 5c by a single or multi-stage pressing operation, during which the originally flat strip 2 is folded in several layers 8 forming several folds 16, 17. The turning or folding takes place in a zig-zag shape, more or less in the cross-sectional shape of a "W". The edge length L (FIG. 3b) of the strip 2 is preserved, i.e. it more or less corresponds to the length of the finished tampon between its insertion end and its rear end.

The folds 16, 17 which are formed right at the start of the shaping process restrict or at least prevent any lateral movement of the withdrawal string 3, as a result of which the thread is not able to slip or disappear during the rest of the process of pressing the strip 2 to the final tampon shape. This advantage is obtained irrespective of the option of welding or bonding the withdrawal string in a preceding production step as described above. Another option is one whereby the sheath 2b is not placed around the material strip 2 until a point at which the withdrawal string 3 has already been placed in the shape of a loop around the respective strip 2.

Once the shaping process is complete, i.e. pressing, the tampon is then inserted in the sleeve of the tampon applicator. Such applicators are known and usually consist of two telescopic, cardboard sleeves.

Compared with the prior art, production times can be improved with the tampon and the method of producing it. For example, in the case of known machines used to manufacture applicator tampons, it is barely possible to produce more than 70 tampons per minute per web of endless material fed through. To produce higher numbers of tampons, it would be necessary to feed several webs of endless material to the machine. By looping round the withdrawal string, these problems are overcome, making it possible to produce up to 120 tampons per minute per endless web and insert them in the co-operating applicators.

List of Reference Numbers

| | |
|---|---|
| 1 | Tampon |
| 2 | Absorbent strip |
| 2a | Wadding strip |
| 2b | Sheath |
| 3 | Withdrawal string |
| 4 | Loop |
| 5 | Endless material |
| 6 | Welding apparatus |
| 6a | Top pressing piece |
| 6b | Bottom pressing piece |
| 7 | Radial pressing jaw |
| 8 | Layer |
| 9 | Knot |
| 10 | Notch, slit |
| 11 | Top face |
| 12 | Bottom face |
| 13 | Cutter |
| 14 | Contact jaw |
| 15 | Contact jaw |
| 16 | Fold |
| 17 | Fold |
| B | Width |
| L | Length |

The invention claimed is:

1. Method of producing a tampon from an absorbent strip joined to a withdrawal string, comprising the following steps:
   a) cutting an absorbent strip with a width and a length which corresponds to an edge length of the absorbent strip and approximately the length of the finished tampon between an insertion end and a rear end;
   b) placing a withdrawal string in a loop around the absorbent strip more or less at the center of the width in the direction of the length before folding the absorbent strip;
   c) knotting the withdrawal string at a rear free end;
   d) folding the absorbent strip, preserving the same length, in a zig-zag shape to form several layers by pressing together jaws of a press which can be moved towards one another, forming folds in the absorbent strip on each side of the loop; and
   e) pressing the absorbent strip via the jaws in a single or multiple-stage pressing operation to an approximately cylindrical shape.

2. Method according to claim 1, wherein the absorbent strip is provided with a sheath.

3. Method according to claim 2, wherein the withdrawal string is joined to the absorbent strip or to the sheath by welding.

4. Method according to claim 2, wherein the withdrawal string is joined to the absorbent strip or to the sheath by bonding.

5. Tampon with an insertion end and a rear end, made from a pressed absorbent strip with a width and a length which corresponds to an edge length of the pressed absorbent strip and to approximately the length of the finished tampon between an insertion end and a rear end, and a withdrawal string running out from the rear end, which withdrawal string is placed in the shape of a loop approximately at the center of the width wrapped around the pressed absorbent strip in the direction of the length and is provided with a knot at a rear free end of the withdrawal string, wherein the pressed absorbent strip is folded, preserving the same length, in a zig-zag shape in several layers between which several folds are formed, and a fold is formed on each side of the loop, and wherein the tampon is produced according to the method as claimed in claim 1.

6. Tampon according to claim 5, wherein the pressed absorbent strip pressed in a zig-zag shape forming the folds is of an essentially cylindrical shape.

7. Tampon according to claim 5, wherein the withdrawal string is clamped by the loop in the region of the point at which the loop is turned back on itself in a short slit or a notch on a face extending in the direction of the length of the pressed absorbent strip.

8. Tampon according to claim 5, wherein the pressed absorbent strip is made up of a fiber or wadding strip suitable for storing liquid and a sheath enclosing the fiber or wadding strip.

9. Tampon according to claim 8, wherein the withdrawal string is joined to the pressed absorbent strip or to the sheath by welding.

10. Tampon according to claim 8, wherein the withdrawal string is bonded to the pressed absorbent strip or to the sheath.

11. Tampon according to claim 9, wherein the withdrawal string is welded or bonded along both a top face of the pressed absorbent strip and along a bottom face of the pressed absorbent strip.

* * * * *

UNITED STATES PATENT AND TRADEMARK OFFICE
CERTIFICATE OF CORRECTION

PATENT NO.         : 8,568,381 B2                                              Page 1 of 1
APPLICATION NO. : 12/451796
DATED              : October 29, 2013
INVENTOR(S)        : Mueller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 799 days.

Signed and Sealed this

Fifteenth Day of September, 2015

Michelle K. Lee
*Director of the United States Patent and Trademark Office*